United States Patent [19]

Denis et al.

[11] Patent Number: 4,857,657
[45] Date of Patent: Aug. 15, 1989

[54] PREPARATION OF HEXENEDIOIC ACID DIESTERS

[75] Inventors: Philippe Denis, Decines; Jean-Marc Frances, Villeurbanne, both of France

[73] Assignee: Rhone-Poulenc Chimie, Courbevoie, France

[21] Appl. No.: 121,283

[22] Filed: Nov. 16, 1987

[30] Foreign Application Priority Data

Nov. 14, 1986 [FR] France .................. 86 16046

[51] Int. Cl.$^4$ .................................. C07C 67/38
[52] U.S. Cl. ............................ 560/193; 502/230; 502/326; 560/190; 560/204; 562/592; 562/595
[58] Field of Search .................. 560/193, 204, 190

[56] References Cited

U.S. PATENT DOCUMENTS

| | | | |
|---|---|---|---|
| 3,309,403 | 3/1967 | Mador et al. | 260/544 |
| 4,166,913 | 9/1979 | Kesling et al. | 560/204 |
| 4,171,450 | 10/1979 | Kesling et al. | 560/204 |
| 4,321,408 | 3/1982 | Mauer et al. | 560/192 |
| 4,386,217 | 5/1983 | Ainbinder et al. | 560/207 |
| 4,552,976 | 11/1985 | Lin et al. | 560/204 |

FOREIGN PATENT DOCUMENTS 987274  3/1965  United Kingdom .

Primary Examiner—Werren B. Lone
Assistant Examiner—Vera C. Clarke
Attorney, Agent, or Firm—Burns, Doane, Swecker & Mathis

[57] ABSTRACT

Hexene-1,6-dioates, readily hydrogenated into adipates (which in turn are conveniently hydrolyzed into adipic acid), are prepared by reacting carbon monoxide, an alcohol and at least one dichlorobutene, in the presence of a catalytically effective amount of palladium or a palladium compound and no more than two equivalents (relative to the dichlorobutene) of a tertiary amine reaction promoter; in an alternate embodiment, the tertiary amine and the dichlorobutene are first converted into a quaternary ammonium chloride intermediate.

30 Claims, No Drawings

PREPARATION OF HEXENEDIOIC ACID DIESTERS

BACKGROUND OF THE INVENTION

1. Field of the Invention:

The present invention relates to the preparation of 1,6-hexenedioic acid diesters. Such diesters can be hydrogenated into the corresponding adipic acid diesters, or adipates, which can in turn be hydrolyzed to form adipic acid. Adipic acid, one of the principal raw materials for nylon 66, is today produced in vast amounts.

More especially, the present invention relates to the preparation of 3-hexenedioic acid diesters by reacting carbon monoxide and an alcohol with a dichlorobutene in the presence of a palladium-based catalyst.

2. Description of the Prior Art:

It is known to this art (cf. *Journal of the American Chemical Society*, 86, p. 4,351 (1964)) that ethyl vinylacetate may be prepared by reacting, at 120° C. under a pressure of approximately 130 atm, carbon monoxide, ethanol and allyl chloride, in the presence of palladium (II) chloride.

It is also well known to this art (cf. *Journal of Organometallic Chemistry*, 188, p. 229 (1980)) that methyl vinylacetate may be produced by reacting, at 80° C. under 200 atm, carbon monoxide, methanol and allyl chloride, in the presence of a catalyst based on bis(triphenylphosphine)palladium (II) chloride and tin (II) chloride in methyl isobutyl ketone or benzene.

However, simply extrapolating these techniques to a substrate such as 1,4-dichloro-2-butene or 3,4-dichloro-1- butene does not provide the desired diesters.

Moreover, a process in which 1,4-diethoxy-2-butene is reacted with carbon monoxide and ethanol in the presence of palladium (II) acetylacetonate and hydrochloric acid, at a temperature of 160.C, the initial pressure of carbon monoxide being 150 kg/cm$^2$, to produce, in particular, the diethyl ester of 3-hexenedioic acid, is described in the Japanese patent application published under No. 68/23,929. However, the selectivity for the 3-hexenedioate remains low, despite relatively severe conditions of temperature, pressure and reaction time (cf. the detailed study by the same authors in *Tetrahedron*, 25, p. 4,189–4,190 (1969)).

Ongoing investigations with a view towards the development of novel techniques for the preparation of adipic acid have demonstrated that serious need exists for an effective method for the preparation of linear diesters of 3-hexenedioic acid, referred to simply as hexene-1,6-dioates, which, after hydrogenation, provide the corresponding adipate. Equally seriously need exists for effective means for the preparation of hexene-1,6-dioates from dichlorobutene, and more particularly from 1,4-dichloro-2-butene, 3,4-dichloro-1-butene or mixtures thereof in all proportions.

Moreover, it too is known to the art that the chlorination of butadiene in the gaseous phase, for example in the presence of catalysts based on palladium and copper, results in the facile and selective formation of a mixture of 1,4-dichloro-2-butene and 1,2-dichloro-3-butene (cf. U.S. Pat. No. 3,823,096).

SUMMARY OF THE INVENTION

Accordingly, a major object of the present invention is the provision of an effective and selective process for the preparation of hexene-1,6-dioates from carbon monoxide, an alcohol and at least one dichlorobutene.

Briefly, the present invention features a process for the preparation of hexene-1,6-dioates by reacting carbon monoxide, an alcohol and at least one dichlorobutene in the presence of a catalytically effective amount of palladium or of a palladium compound, the reaction being assisted or promoted by a tertiary amine, the quantity of which does not exceed two molar equivalents relative to the dichlorobutene.

DETAILED DESCRIPTION OF THE PREFERRED EMBODIMENTS OF THE INVENTION

More particularly according to the present invention, the final product hexene-1,6-dioates have the formula (I):

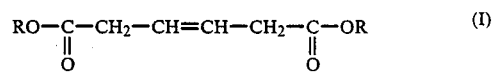

in which R is a straight or branched chain alkyl radical containing a maximum of 12 carbon atoms in the main chain thereof, with the proviso that it may bear one or two alkyl substituents containing a maximum of 4 carbon atoms, or one or two hydroxyl groups; a cycloalkyl radical containing from to 7 carbon atoms; an aralkyl radical containing from 7 to 2 carbon atoms or a phenyl radical.

The radical R is the residue of the alcohol ROH which is one of the reagents required for carrying out the present invention.

By "dichlorobutene" are intended 1,4-dichloro-2-butene, 3,4-dichloro-1-butene and mixtures thereof.

As mentioned above, the reaction is assisted by a tertiary amine. The tertiary amine advantageously has either of the following formulae (II) and (III):

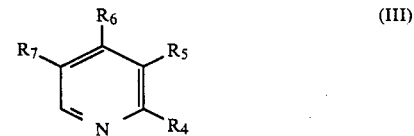

in which $R_1$, $R_2$ and $R_3$, which may be identical or different, are each a straight or branched chain alkyl radical containing from 1 to 16 carbon atoms, optionally substituted with a phenyl group; a straight or branched chain alkenyl radical containing from 2 to 12 carbon atoms, preferably from to 8 carbon atoms; an aryl radical containing from 6 to 10 carbon atoms, optionally substituted with one or two alkyl radicals containing from 1 to 4 carbon atoms; with the proviso that two of the said radicals $R_1$ to $R_3$ may together form a straight or branched chain alkylene, alkenylene or alkadienylene radical containing from 3 to 6 carbon atoms, or a group formed from two alkylene radicals, which can be identical or different, containing from 1 to 3 carbon atoms and linked to each other via an oxygen or sulfur atom; with the further proviso that the three radicals $R_1$ to $R_3$ may together form, with the nitrogen atom from which they depend, a heterocycle containing two ortho-fused rings, the nitrogen atom being common to the two rings; and also with the proviso that the three radicals $R_1$ to $R_3$ may together form, with the nitrogen atom from which they depend, a heterocycle containing a carbon-nitrogen double bond, and, optionally, a carbon-carbon double bond which may be common to the heterocycle and to a benzene ring; and further in which $R_4$, $R_5$, $R_6$ and $R_7$, which also may be identical or different, are each a hydrogen atom; a straight or branched chain alkyl radical containing from 1 to 4 carbon atoms; with the proviso that two of the radicals $R_4$ to $R_7$, borne by adjacent carbon atoms of the ring, may together form an alkylene, alkenylene or alkadienylene radical containing four carbon atoms, or a group formed from two alkylene radicals, which can be identical or different, containing from 1 to 3 carbon atoms and linked to each other via an oxygen or sulfur atom.

Exemplary of the tertiary amines which are useful according to the present invention, representative are:
Trimethylamine
Triethylamine
Tri(n-butyl)amine
Di(isopropyl)ethylamine
Benzyldimethylamine
Methyldiphenylamine
Dimethylphenylamine
Ethylmethylphenylamine
Methyl(n-propyl)phenylamine
Ethylphenylpropylamine
Diethylphenylamine
Di(n-propyl)phenylamine
N-ethylmorpholine
N-methylpyrrolidine
Indolizine
2H-pyrrole
3H-indole
Pyridine
2-(or 4-)Picoline
3,5-Lutidine
Isoquinoline
Quinoline A first category of tertiary amines suitable for carrying out the present invention corresponds to formula (II) above.

Preferred among such tertiary amines are those wherein at least one of the radicals $R_1$ to $R_3$ is an unsubstituted straight chain alkyl or alkenyl radical, or wherein one of the radicals $R_1$ to $R_3$ is an aryl radical, and the other two, which can be identical or different, are unsubstituted straight chain alkyl radicals. The radicals $R_1$ to $R_3$ are advantageously identical and selected from among straight chain alkyl radicals containing a maximum of 4 carbon atoms. In this first category of tertiary amines, triethylamine is more particularly preferred.

A second category of tertiary amines suitable for carrying out the present process corresponds to formula (III) above.

Preferred among such latter tertiary amines are those wherein two of the radicals $R_4$ to $R_7$ are hydrogen atoms and the other two radicals, which may be identical or different, are straight chain alkyl radicals containing a maximum of 4 carbon atoms, with the proviso that these two radicals, when they are borne by adjacent carbon atoms of the ring, may together form an alkylene, alkenylene or alkadienylene radical containing 4 carbon atoms, or a group formed from two ethylene radicals linked to each other via an oxygen atom.

In this second category of tertiary amines, pyridine is more particularly preferred.

As heretofore mentioned, the subject reaction is assisted by a tertiary amine in that such amine is indispensable for satisfactory progress of the reaction. While it is believed that the subject reaction can be represented by the following reaction equations 1 (a and b) and 2, based on the assumption that the reaction is carried out utilizing 1,4-dichloro-2-butene, methanol and triethylamine, applicants expressly do not limit the scope of their invention thereto, nor do they wish to be bound by the explanations given below:

Equation 1 (a):

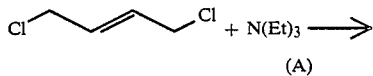

(A)

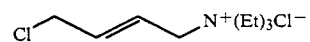

Equation 1 (b):

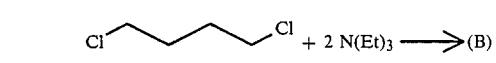

(B): 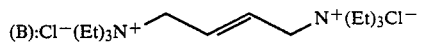

Equation 2:

A and/or B 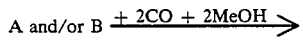

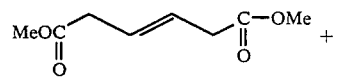

$[HCl + HN^+(Et)_3Cl^-]$ and/or $2[HN^+(Et)_3Cl^-]$

Consistent herewith, it has now been observed, on the one hand, that the quaternary ammonium chloride formed in Equation 1 (a or b) is the same when 3,4-dichloro-1butene is used as a starting material and, on the other, the fundamental role of this quaternary ammonium chloride in the actual alkoxycarbonylation reaction has been demonstrated.

It has also been determined that the desired reaction does not take place when the tertiary amine constitutes more than two equivalents relative to the dichlorobutene employed.

Although the effect of the tertiary amine is significant when it is introduced at a rate of 0.05 mole per mole of dichlorobutene employed, for a much more satisfactory course of reaction, the quantity of tertiary amine will be at least equimolar, within plus or minus 20%, and preferably within plus of minus 10%, of the dichlorobutene.

As shown by the above equations, at least a part of the dichlorobutene is first converted into the quaternary ammonium chloride. This quaternary ammonium chloride, which results from the attachment of one (to two) mole(s) of tertiary amine per mole of dichlorobutene, then becomes the substrate for the reaction by which two RO(CO)-groups, R being as defined above, become attached to the carbon chain derived from the dichlorobutene. These two reactions may be carried out in a single operational stage, or, alternatively, in two separate operations.

In the embodiment employing a single stage, the dichlorobutene, the alcohol, the tertiary amine and the carbon monoxide are reacted, in the presence of a catalyst, in a single reactor. The quaternary ammonium chloride in question is produced in situ under the "alkoxycarbonylation" reaction conditions more fully discussed below.

In the embodiment employing two stages, in a first stage, the quaternary ammonium chloride in question is prepared by reacting the dichlorobutene and the tertiary amine in substantially equimolar proportions. After a reaction time which generally ranges from 30 to 60 minutes, at a temperature on the order of 20° to 50° C., the ammonium salt precipitates; it is then recovered simply by filtering and, where appropriate, purified simply by washing, for example with diethyl ether. It is envisaged to use solvents or diluents during this stage of preparation.

In the second stage, which can be carried out in the same apparatus as the first stage (quaternization phase), on condition, however, that it is pressure-resistant, the reaction is carried out between the quaternary ammonium chloride produced in the first stage (where appropriate, purified by any suitable means, and, optionally, in the presence of an additional amount of tertiary amine, on condition, however, that the total amount employed in the two stages does not exceed the maximum amount set forth hereinbefore), the alcohol and the carbon monoxide, in the presence of the palladium catalyst.

The "alkoxycarbonylation" reaction conditions will be described below.

Irrespective of whether a single-stage or a two-stage operation is selected, the reaction by which two RO(CO)-groups, R being as above defined, become attached to the carbon chain derived from dichlorobutene (which reaction is referred to simply as "alkoxycarbonylation") is carried out in a liquid phase in the presence of a catalytically effective amount of palladium or of a palladium compound.

The reaction is advantageously carried out using palladium which has a degree or state of oxidation of (II) or zero (0), the major part of which is soluble in the medium and under the reaction conditions.

As specific examples of palladium (II) or (0) compounds suitable for carrying out the process of the invention, representative are:
(i) Organic acid salts, such as palladium (II) acetate, palladium (II) formate, palladium (II) propionate, palladium (II) octanoate and palladium (II) ethylhexanoate;
(ii) Inorganic acid salts such as palladium (II) nitrate and chloride;
(iii) $\pi$-Allyl complexes of palladium (II), such as chloro($\pi$-allyl)palladium;
(iv) Palladium (II) acetylacetonate;
(v) Complexes of palladium and a trialkyl- or triarylphosphine, such as tetrakis(triphenylphosphine)palladium; and
(vi) Compounds of palladium (0) and dibenzylideneacetone (dba); Pd(dba)$_2$, Pd$_2$(dba)$_3$, Pd(dba)$_3$ and mixtures thereof.
Bis(dibenzylideneacetone)palladium and palladium chloride are more especially preferred.

The amount of palladium to be employed according to the invention may vary over wide limits. In practice, this amount will be selected such that the process is economically advantageous.

The high activity of the palladium catalysts permits them to be employed in very small amounts (corresponding to a molar ratio palladium: optionally quaternized dichlorobutene on the order of 0.01:100). The use of a large amount of catalyst (corresponding to a molar ratio palladium: optionally quaternized dichlorobutene on the order of 10:100) is not deleterious. Nonetheless, given the premise that the object of the invention is to provide an alkoxycarbonylation reaction which is sufficiently rapid and selective, without having to use an exorbitant amount of palladium, a palladium: optionally quaternized dichlorobutene ratio ranging from 0.5:100 to 5:100 is generally preferable.

The alkoxycarbonylation reaction requires the use of an alcohol of the formula ROH, with R being as defined above.

Exemplary of alcohols which can be employed in the process of the invention, representative are methanol, ethanol, isopropanol, n-propanol, tert-butanol, n-hexanol, cyclohexanol, 2-ethyl-1-hexanol, 1-dodecanol, ethylene glycol, hexane-1,6-diol, benzyl alcohol, phenylethyl alcohol and phenol.

An alkanol containing a maximum of 4 carbon atoms is preferably employed; methanol and ethanol are especially well suited for conducting the subject process.

The alkoxycarbonylation reaction, by virtue of the stoichiometry thereof, requires two moles of alcohol per mole of substrate, the term "substrate" referring in this case to the dichlorobutene or the quaternary ammonium chloride formed in accordance with the principle illustrated in reaction equation (1). Nevertheless, the amount of alcohol may vary over wide limits.

Thus, although it is possible to use from 0.5 to 10 times the amount of alcohol stoichiometrically required, in order to achieve a maximum conversion of the substrate and to avoid, at the same time, an excessive dilution of the reaction medium by the alcohol, it is preferable to carry out the process utilizing a molar ratio alcohol:substrate of from approximately 0.8:1 to 5:1.

The alkoxycarbonylation reaction requires the presence of carbon monoxide. Carbon monoxide is preferably employed in an essentially pure form, such as is commercially available. However, the presence of impurities such as carbon dioxide, oxygen, hydrogen, methane and nitrogen, may be tolerated.

The alkoxycarbonylation reaction is typically carried out at a temperature higher than or equal to 60° C.; it does not appear desirable to exceed a temperature of 160° C., such as to inhibit any reactions giving rise to degradation of the starting materials.

Good results are obtained when the temperature ranges from 70° to 110° C.

The reaction is carried out in the liquid phase at a pressure generally higher than 50 bar, in order to attain an appreciable conversion rate. It is not advantageous to employ pressures as high as 700 bar. For satisfactory conduct of the reaction, a total pressure of 80 to 200 bar is generally preferred.

As illustrated in the above equation 2, methanol and hydrochloric acid are present simultaneously and this can generate water. Since the presence of water is detrimental to the selectivity of the reaction vis-a-vis desired final products, it is advantageous to carry out the alkoxycarbonylation reaction in the presence of a dehydrating agent, for example 2,2-dimethoxypropane.

When the reaction is carried out using an amount of tertiary amine close to the maximum amount mentioned above, all or a part of the hydrochloric acid is immobilized in the form of the hydrochloride corresponding to the amine employed. It then proves unnecessary to introduce a dehydrating agent.

The presence of a solvent or diluent is not essential for carrying out the process according to the invention. However, solvents or diluents, for example chlorinated or non-chlorinated aromatic hydrocarbons, chlorinated alkanes and dimethylformamide, may be employed. In this case, solvents which solubilize the starting materials or the intermediates, such as dimethylformamide or dichloromethane, will preferably be used.

Upon completion of the reaction, the hexene-1,6-dioate produced is separated from the remaining constituents of the reaction mixture by any suitable means, for example by distillation.

The subject process is particularly well suited for the preparation of methyl (or ethyl) 3-hexenedioate.

In order to further illustrate the present invention and the advantages thereof, the following specific examples are given, it being understood that same are intended only as illustrative and in nowise limitative.

In said examples below, the following convention is used:

RY denotes the ratio of the number of moles of final products to the number of moles of starting materials, whether dichlorobutene or quaternized dichlorobutene.

EXAMPLES 1 to 9 control test (a)

A first series of tests was carried out according to the following procedure.

The following materials were introduced (unless otherwise indicated) into a 125 cm$^3$ HASTELLOY B2$^R$ stainless steel autoclave which had previously been purged with argon:
(i) 6.25 g (50 mmol) of 1,4-dichloro-2-butene;
(ii) 15 g (469 mmol) of methanol;
(iii) 1.25 milligram-atom of palladium, in the form of PdCl$_2$ [or Pd(dba)$_2$ in the examples marked with an "x"]; and
(iv) where appropriate, a tertiary amine, the nature and the amount of which are indicated below.

The autoclave was closed airtight, placed in an agitated oven and connected to a gas supply under pressure. bar of carbon monoxide were admitted in the cold state and the contents were heated to 95° C. When this temperature was reached, the pressure was adjusted to 120 bar. After a reaction period (t), the autoclave was cooled and returned to atmospheric pressure. The reaction solution was filtered and then analyzed by gas chromatography. The products formed were essentially:
(a) Methyl 3-hexenedioate (3HD)
(b) Methyl pentenoates (3P)
(c) Methyl pentadienoate (PD)

The particular reaction conditions and the results obtained are reported in the Table I which follows:

TABLE I

| Example No. | Tertiary amine | | Time period | RY (in %) | | |
|---|---|---|---|---|---|---|
| | Nature | mmol | | 3HD | 3P | PD |
| 1 | triethylamine | 50 | 1 hr, 15 min | 8.5 | 3.5 | 0.5 |
| 2 (x) | pyridine | 33 | 1 hr, 50 min | 8.5 | ND | 0.6 |
| 3 (x) | triethylamine | 50 | 1 hr, 20 min | 7.5 | 25 | 2.5 |
| 4 (xx) | triethylamine | 50 | 1 hr, 30 min | 7.5 | 28.5 | 1.5 |
| 5 | N—ethylmorpholine | 50 | 1 hr, 50 min | 7 | 28 | 1.2 |
| 6 | tributylamine | 50 | 3 hr | 4.5 | 47 | 0 |
| 7 | 3,5-lutidine | 50 | 1 hr, 50 min | 15.5 | 12 | 11 |
| 8 | N—methylpyrrolidine | 50 | 50 min | 8.5 | 8.5 | 18 |
| 9 | N—methylpyrrolidine | 100 | 2 hr | 11.1 | 0.5 | 27.5 |
| a (xxx) | none | 0 | 1 hr, 30 min | 0 | — | — |

(x) = Pd(dba)$_2$
(xx) = 5 mg-at of palladium
(xxx) = at the end of the experiment, the following were determined by analysis:
(i) 2.8 mmol of methyl pentanoates and methylbutenoates;
(ii) 25 mmol of methyl pentenoates and methylbutenoates; and
(iii) 0 mmol of 1,4-dichloro-2-butene.

Test (a) evidenced that, in the absence of tertiary amine, the desired reaction did not take place.

EXAMPLES 10 to 15

A second series of tests was carried out in the apparatus and essentially according to the procedure of the preceding examples, except that the introduction of the carbon monoxide at a pressure of 50 bar was preceded by a heating step at 50° C. for a period of time $t_1$, the reaction time period in the presence of carbon monoxide being designated as $t_2$. The charges were in conformity with those described above.

The particular reaction conditions and the results obtained are reported in Table II below:

TABLE II

| Example No. | Amine | mmol | $t_1$ | $t_2$ | RY (in %) | | |
|---|---|---|---|---|---|---|---|
| | | | | | 3HD | 3P | PD |
| 10 | triethylamine | 50 | 1 hr, 30 min | 1 hr, 30 min | 21 | 12.5 | 7.2 |
| 11 | triethylamine | 70 | 2 hr | 1 hr, 30 min | 32.5 | 5.2 | 8 |
| 12 | triethylamine | 90 | 2 hr | 2 hr, 45 min | 36.5 | 3.1 | 13 |
| 13 | triethylamine | 90 | 4 hr | 10 hr | 35 | ND | 13 |
| 14 | pyridine | 70 | 1 hr, 30 min | 3 hr | 44 | 6.3 | 2.5 |
| 15 | pyridine | 70 | 45 min | 3 hr | 45 | 6.1 | 4.6 |

EXAMPLES 16 to 25

A third series of tests was carried out in the apparatus and essentially according to the procedure of Examples 1 to 9, except that the 1,4-dichlorobutene in the charge was replaced by an equivalent amount of (4-chloro-2- butenyl)triethylammonium chloride. Certain tests relate to a charge in which 11 g of methanol were replaced by a solvent, the nature and the amount of which are given below.

The particular reaction conditions and the results obtained are reported in Table III below:

TABLE III

| Example No. | Amine Nature | mmol | Solvent Nature | g | Time Period | RY (in %) 3HD | 3P | PD |
|---|---|---|---|---|---|---|---|---|
| 16 | — | 0 | — | 0 | 1 hr, 20 min | 52.5 | 6 | 6.5 |
| 17 | triethylamine | 40 | — | 0 | 1 hr, 50 min | 27.5 | 2.5 | 17.5 |
| 18 | pyridine | 40 | — | 0 | 2 hr, 15 min | 63.3 | 2 | 8 |
| 19 | N—methylpyrrolidine | 40 | — | 0 | 2 hr, 10 min | 29.3 | 2.8 | 22 |
| 20 | tributylamine | 40 | — | 0 | 2 hr, 10 min | 35.7 | 3.4 | 22 |
| 21 | pyridine | 45 | — | 0 | 2 hr, 20 min | 63.5 | 1.75 | 12.8 |
| 22 | — | 0 | $CH_2Cl_2$ | 21 | 3 hr, 50 min | 11.7 | 16.2 | 0 |
| 23 | — | 0 | DMF | 15 | 2 hr, 30 min | 37.1 | 8.0 | 0 |
| 24 | — | 0 | $CH_3CN$ | 12.5 | 3 hr, 30 min | 28.2 | 16 | 0 |
| 25 | — | 0 | MCB | 21 | 3 hr, 20 min | 14.7 | 21.5 | 0 |

MCB = monochlorobenzene;
DMF = dimethylformamide

EXAMPLES 26 to 34

A fourth series of tests was carried out in the apparatus described above, using a charge containing:
(i) 50 mmol of (4-chloro-2-butenyl)triethylammonium chloride;
(ii) 10 g of methanol;
(iii) 1.25 mg-at of palladium in the form of $PdCl_2$ [except in Example 29, in which it was charged in the form of $Pd(dba)_2$];
(iv) 10 g of dimethoxypropane (except in Example 26, in which only 5 g were used).

The procedure utilized was either that described for the first series of tests (preheating carried out in the presence of carbon monoxide) and indicated by (I) below, or that described for the second series of tests (the introduction of carbon monoxide at 50 bar pressure was preceded by a preheating step at 95° C.) and indicated by (II) below.

The particular reaction conditions and the results obtained are reported in Table IV below:

EXAMPLES 35 to 37

A fifth series of tests was carried out in the apparatus and according to the procedure described for the first series of tests, the charge containing:
(i) 50 mmol of 1,4-bis(triethylammonio)-2-butene chloride;
(ii) methanol;
(iii) where appropriate, dimethoxypropane (DMP); and
(iv) 1.25 mg-at of palladium in the form of $PdCl_2$ (Examples 35 and 37), or of $Pd(dba)_2$ (Example 36).

The particular reaction conditions and the results obtained at 95° C. under 120 bar of carbon monoxide are reported in Table V below:

TABLE V

| Example No. | MeOH (g) | Miscellaneous | t | $R^Y$ (in %) 3HD | 3P | PD |
|---|---|---|---|---|---|---|
| 35 | 10 | Pd(2) | 2 hr, 20 min | 51.0 | 1.5 | 11 |
| 36 | 15 | Pd(o) | 1 hr, 40 min | 42.2 | 2.6 | 1.5 |
| 37 | 12 | Pd(2) + 8.5 g DMP | 3 hr, 40 min | 65.0 | 8.5 | 6.7 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a hexene-1,6-dioate, comprising alkoxycarbonylating at least one dichlorobutene with carbon monoxide and an alcohol, in the presence of a catalytically effective amount of palladium or a palladium compound and no more than about two equivalents, relative to the chlorobutene, of a tertiary amine reaction promoter.

TABLE IV

| Example No. | | T °C. | P (Bars) | t | RY (in %) 3HD | 3P | PD |
|---|---|---|---|---|---|---|---|
| 26 (x) | (I) | 95 | 120 | 1 hr, 40 min | 65.6 | 10.4 | 3.5 |
| 27 | (I) | 95 | 120 | 2 hr, 20 min | 72 | 7.1 | 6.15 |
| 28 | (II) | 95 | 120 | 2 hr | 76.5 | 8.5 | 8.5 |
| 29 (xx) | (II) | 95 | 120 | 2 hr, 30 min | 71.6 | 9.0 | 6.2 |
| 30 | (II) | 95 | 80 | 3 hr, 30 min | 62 | 5.9 | 9.6 |
| 31 | (II) | 95 | 160 | 1 hr, 30 min | 82 | 9.0 | 6.6 |
| 32 | (II) | 95 | 200 | 1 hr, 40 min | 76.7 | 7.0 | 7.0 |
| 33 (xxx) | (II) | 80 | 160 | 4 hr | 86 | 9.0 | 6.5 |
| 34 | (I) | 110 | 160 | 1 hr, 30 min | 70.5 | 7.8 | 5.5 |

(x) = 5 g of dimethoxypropane
(xx) = $Pd(dba)_2$
(xxx) = T : 80° C.; followed by 95° C.

2. The process as defined by claim 1, wherein said at least one chlorobutene and said tertiary amine comprise a quaternary ammonium chloride thereof.

3. The process as defined by claim 2, comprising, a first stage, quaternizing said at least one chlorobutene and said tertiary amine, and then, in a second stage, alkoxycarbonylating the quaternary ammonium chloride thus produced with the carbon monoxide and the alcohol, in the presence of the catalytically effective amount of palladium or a palladium compound and wherein said two stages the total amount of tertiary amine present is no more than about two equivalents relative to said chlorobutene.

4. The process as defined by claim 3, comprising first separating said quaternary ammonium chloride from the medium of quaternization prior to the alkoxycarbonylation second stage.

5. The process as defined by claim 1, carried out in the presence of about one equivalent of tertiary amine, plus or minus up to 20%.

6. The process as defined by claim 5, carried out in the presence of about one equivalent of tertiary amine, plus or minus up to 10%.

7. The process as defined by claim 1, carried out in the liquid phase.

8. The process as defined by claim 1, said tertiary amine having the following formula (II):

in which $R_1$, $R_2$ and $R_3$, which may be identical or different, are each a straight or branched chain alkyl radical containing from 1 to 16 carbon atoms, or a phenyl substituted such radical; a straight or branched chain alkenyl radical containing from 2 to 12 carbon atoms; an aryl radical containing from 6 to 10 carbon atoms, or a substituted such aryl radical bearing one or two alkyl substituents containing from 1 to 4 carbon atoms; with the proviso that two of the said radicals $R_1$ to $R_3$ may together form a straight or branched chain alkylene, alkenylene or alkadienylene radical containing from 3 to 6 carbon atoms, or a group formed from two alkylene radicals, which may be identical or different, containing from 1 to 3 carbon atoms and linked to each other via an oxygen or sulfur atom; with the further proviso that the three radicals $R_1$ to $R_3$ may together form, with the nitrogen atom from which they depend, a heterocycle containing two ortho-fused rings, the nitrogen atom being common to the two rings; and also with the proviso that the three radicals $R_1$ to $R_3$ may together form, with the nitrogen atom from which they depend, a heterocycle containing a carbon-nitrogen double bond.

9. The process as defined by claim 1, said tertiary amine having the following formula (III):

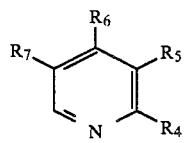

in which $R_4$, $R_5$, $R_6$ and $R_7$, which may be identical or different, are each a hydrogen atom; a straight or branched chain alkyl radical containing from 1 to 4 carbon atoms; with the proviso that two of the radicals $R_4$ to $R_7$, borne by adjacent carbon atoms of the ring, may together form an alkylene, alkenylene or alkadienylene radical containing four carbon atoms, or a group formed from two alkylene radicals, which may be identical or different, containing from 1 to 3 carbon atoms and linked to each other via an oxygen or sulfur atom.

10. The process as defined by claim 8, wherein the formula (II) at least one of the radicals $R_1$ to $R_3$ is an unsubstituted straight chain alkyl or alkenyl radical.

11. The process as defined by claim 8, wherein the formula (II) one of the radicals $R_1$ to $R_3$ is an aryl radical, and the other two, which may be identical or different, are unsubstituted straight chain alkyl radicals.

12. The process as defined by claim 10, wherein the radicals $R_1$ to $R_3$ are each the same unsubstituted straight chain alkyl radical containing up to 4 carbon atoms.

13. The process as defined by claim 12, wherein the tertiary amine is triethylamine.

14. The process as defined by claim 9, wherein the formula (III) two of the radicals $R_4$ to $R_7$ are hydrogen atoms and the other two radicals, which may be identical or different, are straight chain alkyl radicals containing a maximum of 4 carbon atoms, with the proviso that these two radicals, when they are borne by adjacent carbon atoms of the ring, may together form an alkylene, alkenylene or alkadienylene radical containing 4 carbon atoms, or a group formed from two ethylene radicals linked to each other via an oxygen atom.

15. The process as defined by claim 14, wherein the tertiary amine is pyridine.

16. The process as defined by claim 1, wherein the tertiary amine is trimethylamine, triethylamine, tri(n-butyl)amine, di(isopropyl)ethylamine, benzyldimethylamine, methyldiphenylamine, dimethylphenylamine, ethylmethylphenylamine, methyl(n-propyl)phenylamine, ethylphenylpropylamine, diethylphenylamine, di(n-propyl)phenylamine, n-ethylmorpholine, n-methylpyrrolidine, indolizine, 2H-pyrrole, 3H-indole, pyridine, 2-(or 4-) picoline 3,5-lutidine, isoquinoline, or quinoline.

17. The process as defined by claim 1, said hexene-1,6-dioate having the following formula (I):

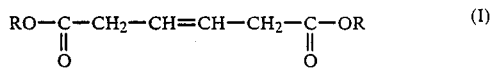

in which R is a straight or branched chain alkyl radical containing a maximum of 12 carbon atoms in the main chain thereof, with the proviso that it may bear one or two alkyl substituents containing a maximum of 4 carbon atoms, or one or two hydroxyl groups; a cycloalkyl radical containing from 5 to 7 carbon atoms; an aralkyl radical containing from 7 to 12 carbon atoms or a phenyl radical.

18. The process as defined by claim 1, carried out in the presence of 0.01 to 10 moles of palladium per 100 moles of chlorobutene.

19. The process as defined by claim 18, carried out in the presence of 0.5 to 5 moles of palladium per 100 moles chlorobutene.

20. The process as defined by claim 1, wherein the palladium catalyst is palladium dichloride or bis(dibenzylideneacetone)palladium.

21. The process as defined by claim 1, wherein the molar ratio alcohol:chlorobutene ranges from 0.5:1 to 10:1.

22. The process as defined by claim 21, said molar ratio ranging from 0.8:1 to 5:1.

23. The process as defined by claim 1, carried out at a temperature of from 60° C. to 160° C.

24. The process as defined by claim 23, carried out under a pressure of more than 50 bar.

25. The process as defined in claim 3, wherein in said second stage alkoxycarbonylation is carried out in the presence of a tertiary amine.

26. The process as defined in claim 8, wherein said heterocycle further comprises a carbon-carbon double bond which may be common to the heterocycle and to a benzene ring.

27. The process as defined in claim 18 wherein said chlorobutene is quaternized.

28. The process as defined in claim 19 wherein said chlorobutene is quaternized.

29. The process as defined in claim 21, wherein said chlorobutene is quaternized.

30. The process as defined in claim 29, said molar ratio ranging from 0.8:1 to 5:1.

* * * * *